US012765872B2

(12) United States Patent
Morin

(10) Patent No.: US 12,765,872 B2
(45) Date of Patent: Oct. 20, 2026

(54) DEVICES AND METHODS FOR THE TREATMENT OF VASCULAR ABNORMALITIES

(71) Applicant: St. Jude Medical, Cardiology Division, Inc., St. Paul, MN (US)

(72) Inventor: Kristen T. Morin, St. Paul, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 52 days.

(21) Appl. No.: 17/554,257

(22) Filed: Dec. 17, 2021

(65) Prior Publication Data

US 2022/0240911 A1 Aug. 4, 2022

Related U.S. Application Data

(60) Provisional application No. 63/143,062, filed on Jan. 29, 2021.

(51) Int. Cl.
*A61B 17/00* (2006.01)

(52) U.S. Cl.
CPC ..................... *A61B 17/0057* (2013.01); *A61B 2017/00477* (2013.01); *A61B 2017/00597* (2013.01); *A61B 2017/00623* (2013.01); *A61B 2017/00628* (2013.01); *A61B 2017/00632* (2013.01); *A61B 2017/00867* (2013.01)

(58) Field of Classification Search
CPC ...... A61B 17/0057; A61B 2017/00477; A61B 2017/00597; A61B 2017/00623; A61B 2017/00628; A61B 2017/00867
See application file for complete search history.

(56) References Cited

U.S. PATENT DOCUMENTS

| | | | | |
|---|---|---|---|---|
| 2004/0143294 | A1 | 7/2004 | Corcoran et al. | |
| 2009/0062841 | A1* | 3/2009 | Amplatz .......... | A61B 17/12159 606/200 |
| 2009/0171386 | A1 | 7/2009 | Amplatz et al. | |
| 2011/0160753 | A1* | 6/2011 | Bastin ............. | A61B 17/12172 606/153 |
| 2012/0071918 | A1* | 3/2012 | Amin ................ | A61B 17/0057 606/213 |
| 2012/0271337 | A1* | 10/2012 | Figulla ............ | A61B 17/12168 87/9 |

(Continued)

OTHER PUBLICATIONS

International Search Report and Written Opinion for International Application No. PCT/US2021/063988, mailed Apr. 5, 2022, 16 pages.

*Primary Examiner* — Kathleen S Holwerda
*Assistant Examiner* — James R Mcginnity
(74) *Attorney, Agent, or Firm* — SLEMAN & LUND LLP

(57) ABSTRACT

Described herein is a medical device including a proximal end and a distal end. The proximal end includes a disc and the distal end includes a lobe. The disc and lobe are connected by a connecting member. The disc includes a proximal surface and a distal surface. The lobe includes a proximal surface, a distal surface, and a side surface extending between and connecting the proximal surface and distal surface of the lobe. The medical device also includes a fabric patch. The fabric patch is coupled to the proximal surface of at least one of the disc or the lobe and to at least one additional surface of the at least one of the disc and the lobe.

17 Claims, 8 Drawing Sheets

(56) References Cited

U.S. PATENT DOCUMENTS

| | | | | |
|---|---|---|---|---|
| 2014/0330303 | A1 | 11/2014 | Hansen | |
| 2015/0005810 | A1 | 1/2015 | Center et al. | |
| 2019/0110796 | A1* | 4/2019 | Jayaraman | A61B 17/12168 |
| 2019/0274668 | A1* | 9/2019 | Glimsdale | A61B 17/12172 |
| 2020/0253615 | A1* | 8/2020 | Melanson | A61N 1/37205 |
| 2023/0210537 | A1* | 7/2023 | Li | A61B 17/12145 606/191 |
| 2024/0050080 | A1* | 2/2024 | Eidenschink | A61B 17/0057 |

* cited by examiner

DEVICES AND METHODS FOR THE TREATMENT OF VASCULAR ABNORMALITIES

CROSS-REFERENCE TO RELATED APPLICATIONS

This application claims the benefit of priority to U.S. Prov. Pat. App. No. 63/143,062 filed Jan. 29, 2021, which is incorporated by reference herein in its entirety.

BACKGROUND OF THE DISCLOSURE

A. Field of Disclosure

The present disclosure relates generally to medical devices that are used in the human body. In particular, the present disclosure is directed to embodiments of an occlusion device that reduce the risk of peri-device leak. More specifically, the present disclosure is directed to an occlusion device with improved fabric patch placement and securement. The embodiments and methods disclosed herein enable increased occlusion after the occlusion device with the fabric patch has been deployed at the target site.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in Left Atrial Appendage (LAA) closures. LAAs are common heart defects in which there is a sac in the muscle wall of the left atrium. When a patient experiences atrial fibrillation (AFib), a blood clot may be formed in the LAA which may become dislodged and enter the blood stream. By occluding the LAA, the release of blood clots from the LAA may be significantly reduced, if not eliminated. Various techniques have been developed to occlude the LAA.

In the case of some known medical devices, a lobed portion of the device sits in a body of the LAA, and a disc portion is engaged with an opening of the LAA. In some known medical devices, a fabric patch is coupled only to a proximal surface of the lobe portion to assist with occlusion of blood flow into the body of the LAA and provide a sealing effect when the lobe portion is fully seated within the body of the LAA. However, the lobe portion of the device may become dislodged or disengaged from the LAA, such that part of the lobe portion is positioned outside of the LAA. In such cases, the sealing effect of the fabric patch is reduced, which may lead to peri-device leakage.

In other known medical devices, the fabric patch is incorporated into the disc portion of the device and is coupled only to the proximal surface of the disc portion. When the medical device is deployed at a target site, tension is exerted between the lobe portion and the disc portion, to pull the distal surface of the disc portion towards the lobe portion (e.g., away from the proximal surface of the disc portion). This tension may cause deformation of the disc portion, such that the edges of the fabric patch are pulled away from the LAA opening, which may lead to peri-device leakage.

It would be advantageous to provide an improved occlusion device that reduces the risk of peri-device leakage.

SUMMARY OF THE DISCLOSURE

The present disclosure is directed to a medical device. The medical device includes a proximal end and a distal end. The proximal end includes a disc and the distal end includes a lobe. The disc and lobe are connected by a connecting member. The disc includes a proximal surface and a distal surface. The lobe includes a proximal surface, a distal surface, and a side surface extending between and connecting the proximal surface and distal surface of the lobe. The medical device also includes a fabric patch. The fabric patch is coupled to the proximal surface of at least one of the disc or the lobe and to at least one additional surface of the at least one of the disc or the lobe.

The present disclosure is also directed to a delivery system for delivering a medical device to a target site. The delivery system includes a medical device including a proximal end and a distal end. The proximal end includes a disc and the distal end includes a lobe. The disc and lobe are connected by a connecting member. The disc includes a proximal surface and a distal surface. The lobe includes a proximal surface, a distal surface, and a side surface extending between and connecting the proximal surface and distal surface of the lobe. The medical device also includes a fabric patch. The fabric patch is coupled to the proximal surface of at least one of the disc or the lobe and to at least one additional surface of the at least one of the disc or the lobe. The delivery system also includes a delivery device coupled to the medical device, the delivery device including a catheter and a delivery cable, wherein the medical device is coupled to the delivery cable, and wherein the delivery cable is configured to be advanced through the catheter to deploy the medical device at the target site.

The present disclosure is further directed to a method for closing a Left Atrial Appendage (LAA). The method includes providing a medical device including a proximal end and a distal end. The proximal end includes a disc and the distal end includes a lobe. The disc and lobe are connected by a connecting member. The disc includes a proximal surface and a distal surface. The lobe includes a proximal surface, a distal surface, and a side surface extending between and connecting the proximal surface and distal surface of the lobe. The medical device also includes a fabric patch. The fabric patch is coupled to the proximal surface of at least one of the disc or the lobe and to at least one additional surface of the at least one of the disc or the lobe. The method includes advancing the medical device to the LAA using a delivery system including a catheter and a delivery cable, positioning the medical device relative to the LAA to occlude blood flow to and from the LAA, and de-coupling the medical device from the delivery cable to deploy the medical device.

BRIEF DESCRIPTION OF THE DRAWINGS

Corresponding reference characters indicate corresponding parts throughout the several views of the drawings. It is understood that that figures are not necessarily to scale.

DETAILED DESCRIPTION OF THE DISCLOSURE

Figure 1:
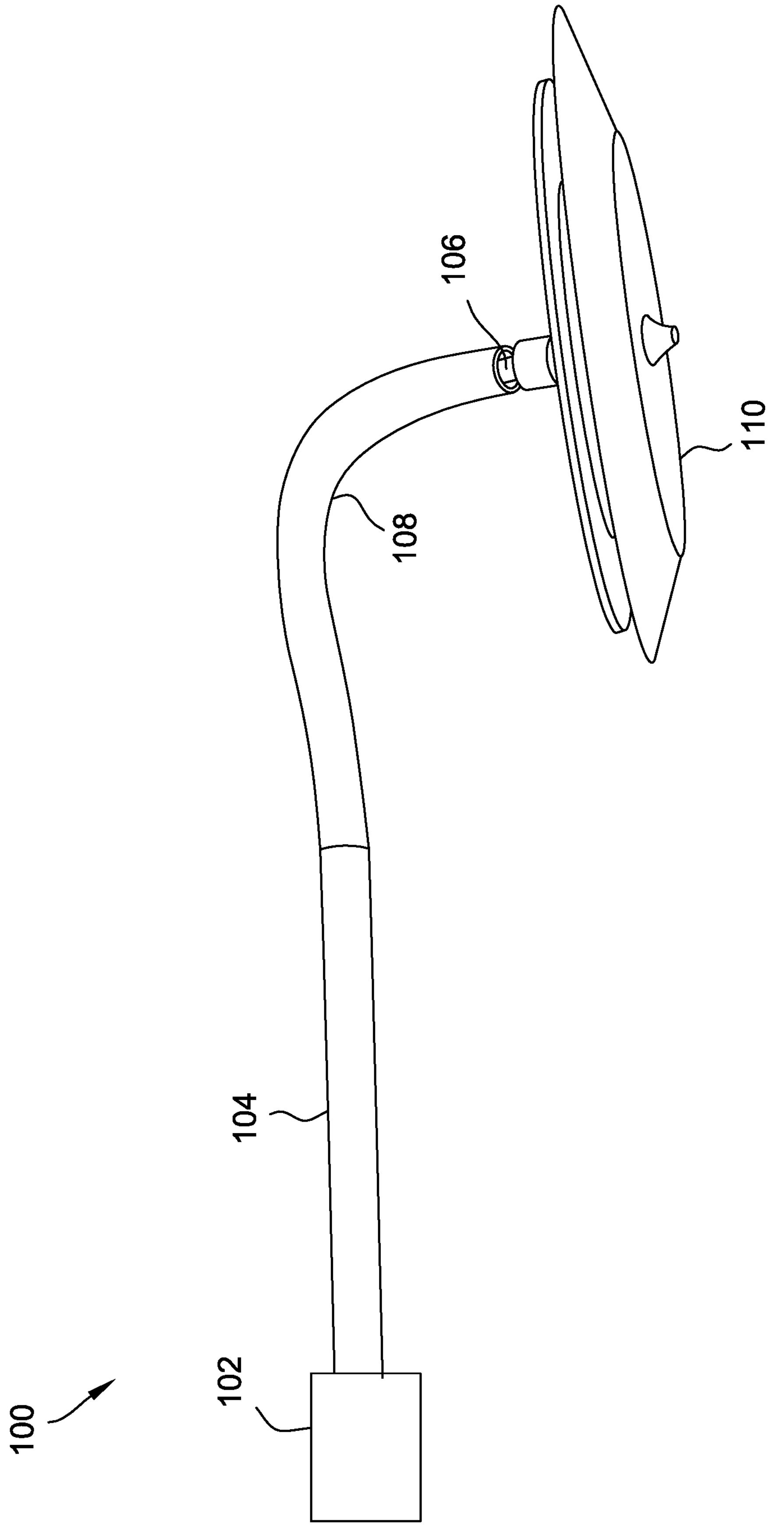
FIG. 1 is a schematic diagram of a delivery system for deploying a medical device at a target site in accordance with the present disclosure.

The present disclosure relates generally to medical devices that are used in the human body. Specifically, the present disclosure provides medical devices, such as occlusion devices, including a distal lobe, a proximal disc, and a fabric patch that extends beyond the proximal surface and is coupled to the lobe and/or the disc.

Accordingly, the occlusion devices of the present disclosure facilitate improved fabric patch configuration, placement, and securement, which enable enhanced sealing between the medical device and patient's vascular system. Therefore, peri-device leakage around the medical device may be reduced or eliminated.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a left atrial appendage (LAA), it is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, an LAA, a lesion, a vessel dissection, or a tumor. Embodiments of the medical device may be useful, for example, for occluding an LAA, patent foreman ovalis (PFO), atrial septal defect (ASD), ventricular septal defect (VSD), or patent ductus arteriosus (PDA), as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as a left atrial appendage. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

The present disclosure is directed to various embodiments of medical devices including fabric patches that are additions and/or alternatives to conventional fabric patches included in known medical devices, to resolve the above-described potential disadvantages of known medical devices. The fabric patches of the present disclosure may be coupled to the proximal surface of at least one of the disc or the lobe and to at least one additional aspect or surface of the at least one of the disc or the lobe, providing increased coverage of the medical device by the fabric patch and enhanced sealing between the medical device and the patient's vascular system.

Turning now to FIG. 1, a schematic diagram of a delivery system 100 is shown. Delivery system 100 includes a delivery device 102 including a catheter 104 and a coupling member 106 configured to couple a distal end of a delivery cable 108 to a medical device 110 for facilitating the deployment of medical device 110 at a target site. Medical device 110 is deployed to treat the target site, and, in the example embodiment, is an occlusion device ("occluder").

Figure 2:
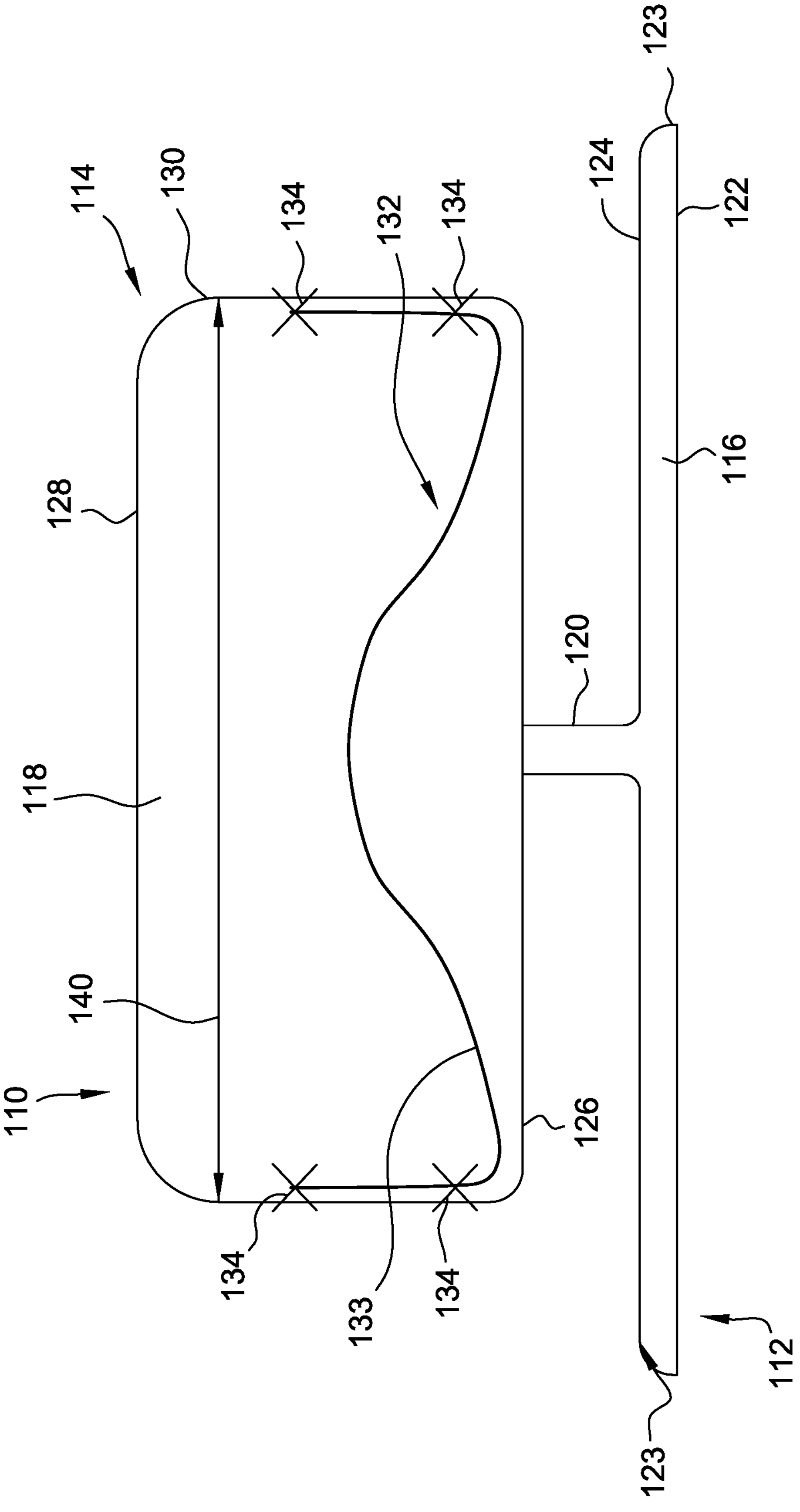
FIG. 2 is a schematic diagram of a medical device in accordance with the present disclosure, the medical device including a fabric patch coupled to a lobe portion thereof.

FIG. 2 illustrates a side view of an exemplary embodiment of medical device 110. Medical device 110 includes a proximal end 112 and a distal end 114, wherein proximal end 112 includes a disc 116 and distal end 114 includes a lobe 118. Disc 116 and lobe 118 are connected by a connecting member 120 (e.g., a waist). Disc 116 includes a proximal surface 122, a distal surface 124, and a side surface 123 (also referred to as an "edge") extending between and connecting proximal surface 122 and distal surface 124. Lobe 118 includes a proximal surface 126, a distal surface 128, and a central or side surface 130 extending between and connecting proximal surface 126 and distal surface 128. In the exemplary embodiment, medical device 110 also includes a fabric patch 132, wherein fabric patch 132 is coupled to at least one of proximal surface 122 and proximal surface 126 of disc 116 and lobe 118, respectively. Fabric patch 132 is also coupled to at least one additional aspect or surface of disc 116 and/or lobe 118. Fabric patch 132 is coupled to disc 116 and/or lobe 118 by sutures 134. In other embodiments, fabric patch 132 is coupled to disc 116 and/or lobe 118 by adhesive, welding, melting, alternative fasteners, and/or using any other suitable attachment method or component. In some embodiments, fabric patch 132 is additionally coupled to connecting member 120.

In the particular embodiment of FIG. 2, fabric patch 132 is coupled to proximal surface 126 of lobe 118, and to side surface 130 of lobe 118. Fabric patch 132 is coupled to side surface 130 of lobe 118 by sutures 134 at various locations about a circumference of lobe 118. For example, sutures 134 are arranged along an outer profile 133 of fabric patch 132 (e.g., at the same or varying axial positions on side surface 130).

Figure 3:
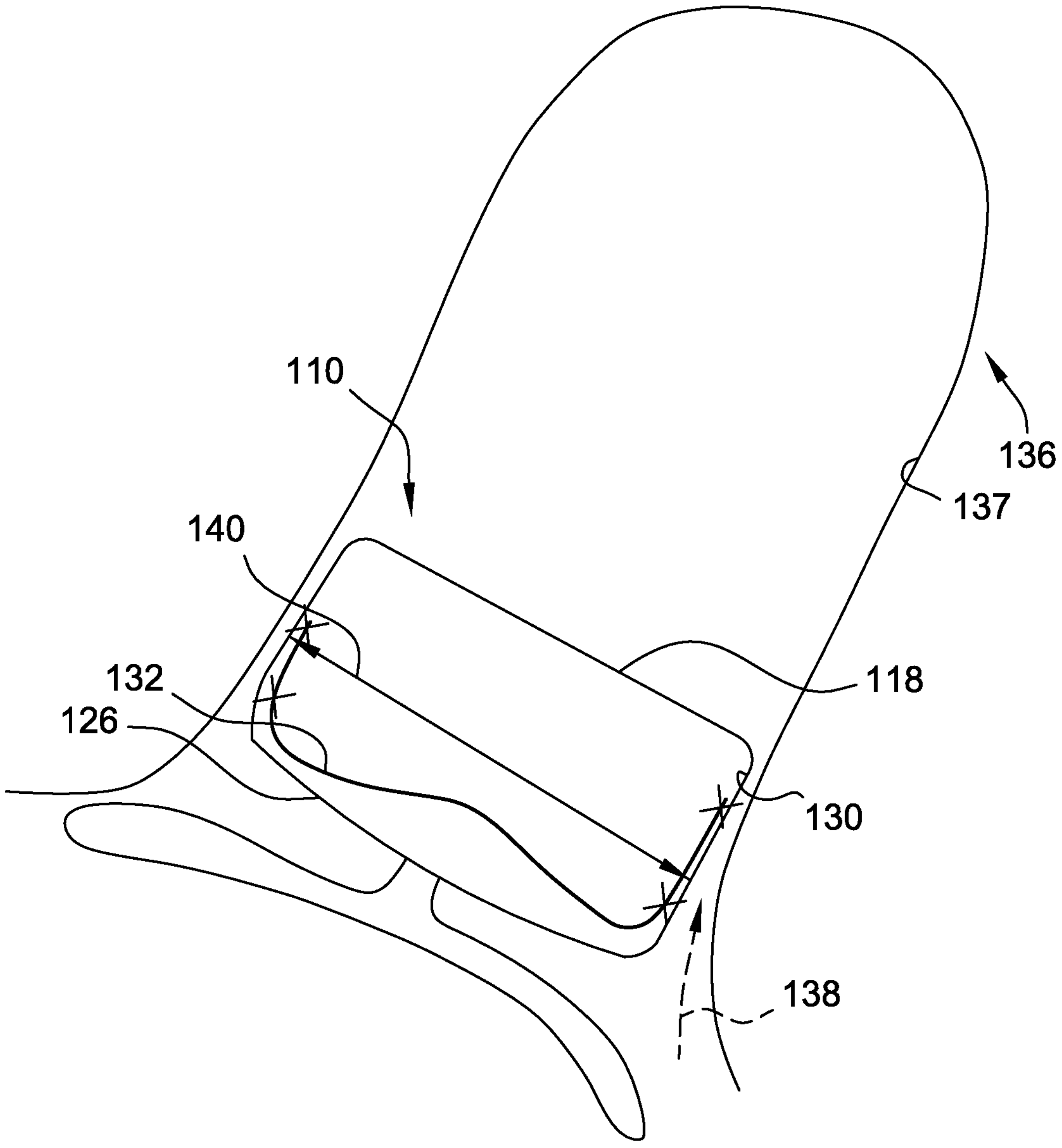
FIG. 3 is a schematic diagram of the medical device of FIG. 2 deployed at a target site.

Turning now to FIG. 3, depicted is a schematic diagram of medical device 110 as shown in FIG. 2—in which fabric patch 132 is coupled to proximal and side surfaces 126, 130 of lobe 118—deployed at a target site 136 (e.g., an LAA). As shown in FIG. 3, in some instances, when medical device 110 is utilized for the occlusion of target site 136, medical device 110 may become dislodged or disengaged from the LAA 136. For example, lobe 118 may partially disengage from a body 137 of the LAA. With medical device 110 of the present disclosure, fabric patch 132 coupled to proximal surface 126 and side surface 130 of lobe 118 provides for increased coverage of lobe 118. That is, a greater portion of lobe 118 (e.g., of side surface 130) is covered by fabric patch 132. The increased coverage of lobe 118 by fabric patch 132 enhances sealing effect between medical device 110 and target site 136, and may effectively reduce or eliminate peri-device leakage pathways 138.

In the embodiment of FIGS. 2 and 3, fabric patch 132 is substantially circular in shape, and has a diameter greater than a diameter 140 of lobe 118. In the exemplary embodiment, the diameter of fabric patch 132 is about 2 mm to about 15 mm larger that diameter 140 of lobe 118 It is contemplated that fabric patch 132 may have any size or configuration that allows for the coupling of fabric patch 132 to proximal surface 126 and side surface 130 of lobe 118. Fabric patch 132 may extend along only a portion of side surface 130 or may extend along the entire axial length of side surface 130 to abut distal surface 128.

Figure 4:
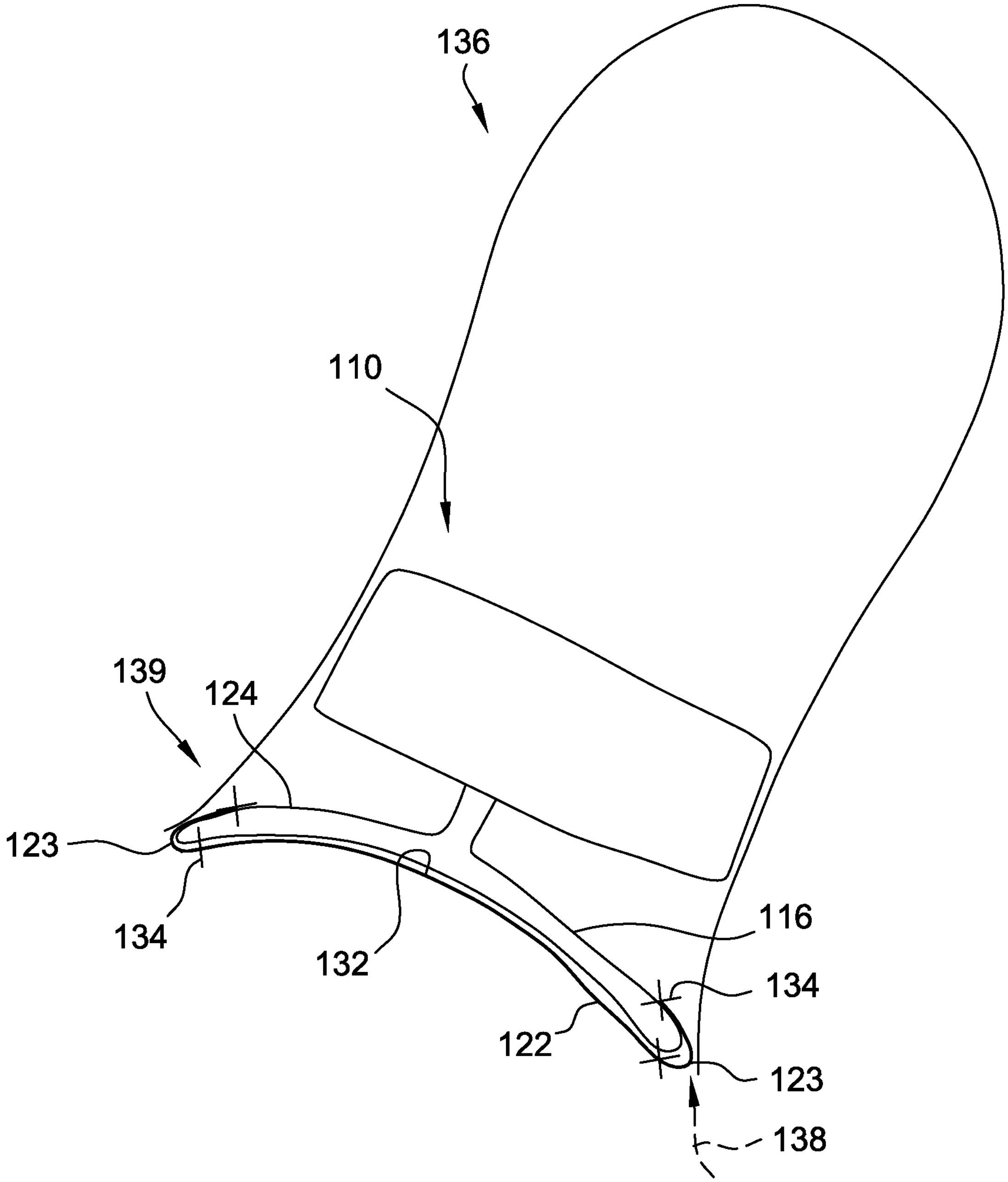
FIG. 4 is a schematic diagram of another medical device in accordance with the present disclosure deployed at a target site, the medical device including a fabric patch coupled to a disc portion thereof.

Turning now to FIG. 4, a schematic diagram of another embodiment of a medical device 110—deployed at a target site 136 (e.g., an LAA)—of the present disclosure is depicted. In this embodiment, fabric patch 132 is coupled to disc 116. Specifically, fabric patch 132 is coupled to proximal surface 122 of disc 116, extends along edge 123 of disc 116, and is coupled to distal surface 124 of disc 116; fabric patch 132 is secured to at least proximal surface 122 and distal surface 124 by sutures 134. In some embodiment, fabric patch 132 is further secured to edge 123 by sutures 134. In this configuration, fabric patch 132 provides substantially continuous coverage from proximal surface 122 to distal surface 124 of disc 116. The continuous coverage eliminates the void of fabric patch 132 along the connection between proximal surface 122 and distal surface 124 (i.e., edge 123), thereby effectively reducing or eliminating peri-device leakage pathway 138 (e.g., across the edge of the disc in some known medical devices) at an opening 139 of LAA 136.

Figure 5B:
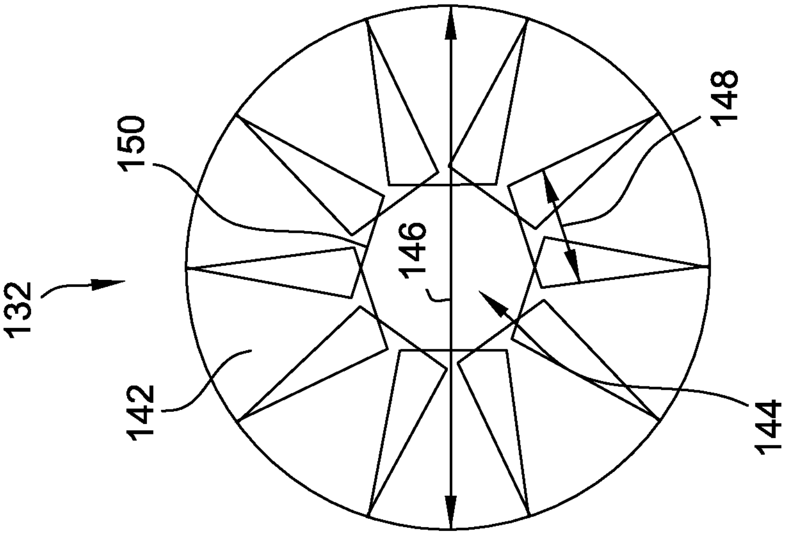
FIGS. 5A and 5B depict additional and/or alternative fabric patches for use with the medical devices of the present disclosure.
Figure 5A:
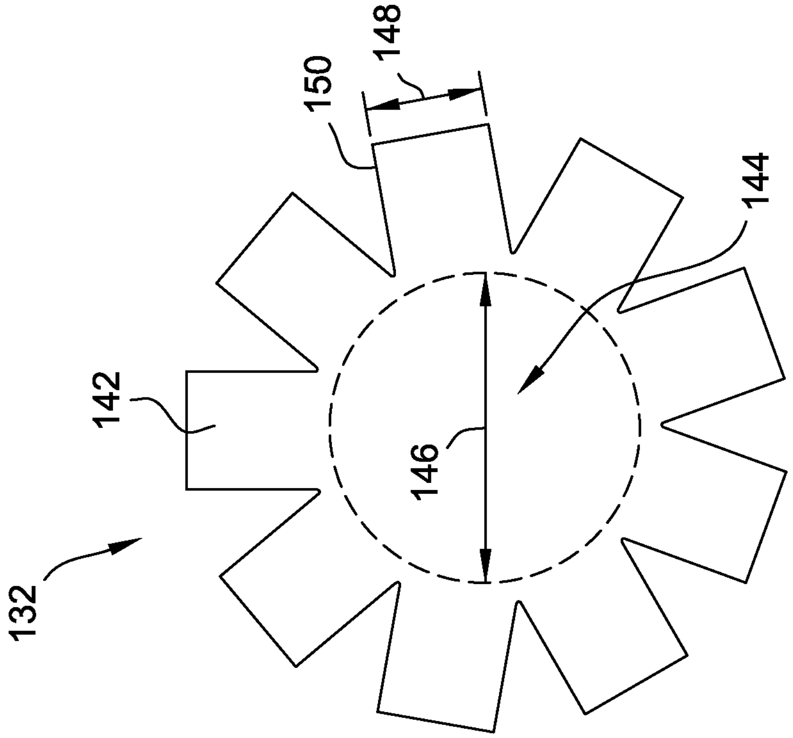

Medical device 110 as shown in FIG. 4 may include a fabric patch 132 as illustrated in FIGS. 5A and 5B. In particular, in some embodiments, fabric patch 132 has a star configuration including a plurality of extensions 142 extending radially outwardly from a central portion 144. Central portion 144 may have a diameter 146 approximately equal to a diameter of disc 116 of medical device 110. Alternatively, diameter 146 may be selected such that central portion 144 extends around edge 123 of disc 116 when fabric patch 132 is coupled to disc. In some embodiments, central portion 144 is coupled to proximal surface 122 and/or edge 123 of disc 116 by sutures 134. Extensions 142 are configured to extend (e.g., fold) around edge 123 of disc 116 and are coupled to distal surface 124 of disc 116 by sutures 134. Extensions 142 each have a width 148 at a terminal end 150 thereof. Width 148 of extensions 142 may be selected to ensure a desired amount of overlap between adjacent extensions 142 when extensions are in the folded position (see FIG. 5B) and coupled to distal surface 124 of disc 116.

Figure 6:
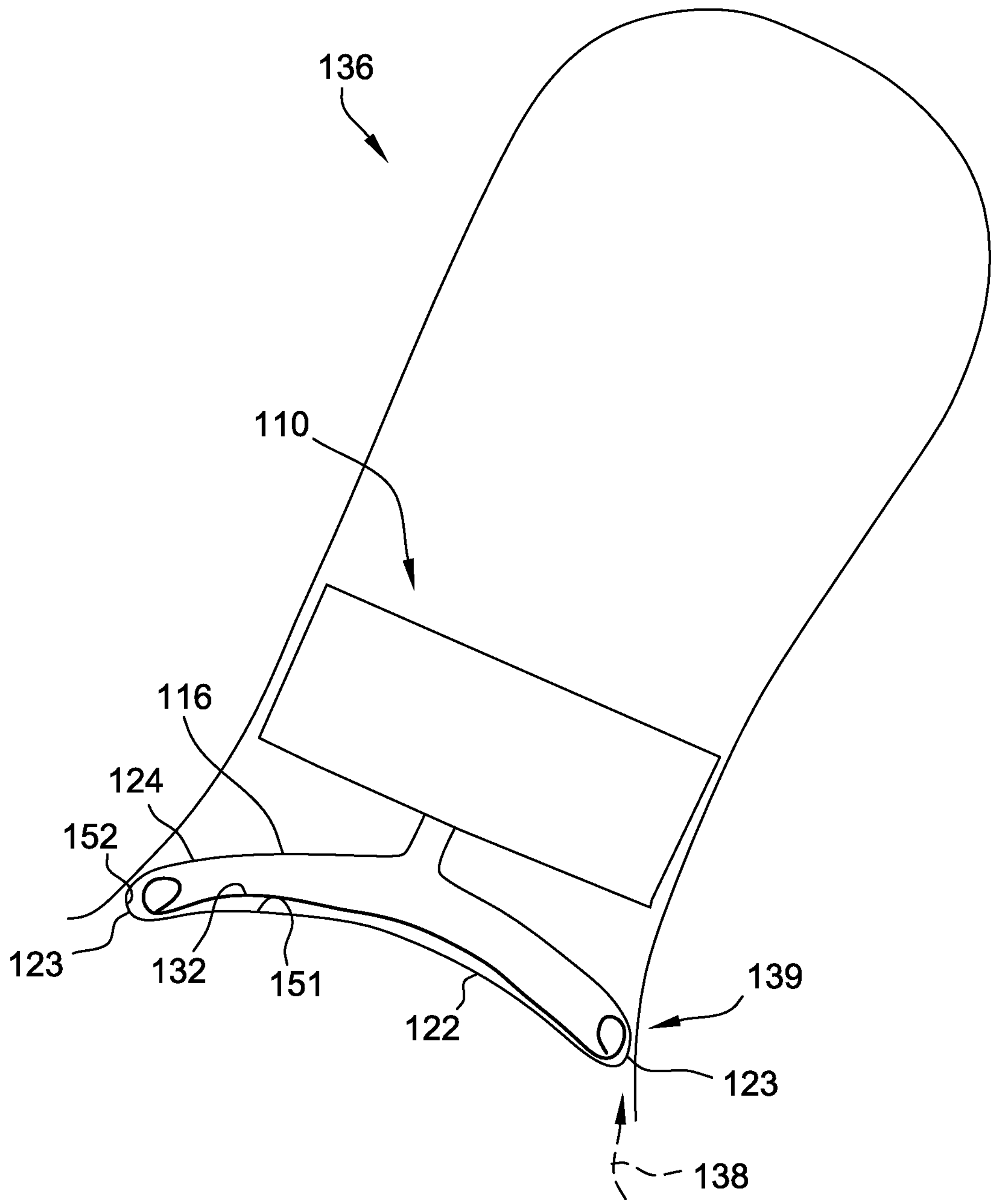
FIG. 6 is a schematic diagram of another medical device in accordance with the present disclosure deployed at a target site, the medical device including a fabric patch coupled to the disc portion thereof.

Turning now to FIG. 6, a schematic diagram of yet another medical device 110—deployed at a target site 136 (e.g., an LAA)—of the present disclosure is depicted. In this embodiment, fabric patch 132 is coupled to an interior surface 151 of proximal surface 122 of disc 116 and to an interior surface 152 of edge 123 disc 116. Coverage of interior edge surface 152 facilitates enhanced sealing effect between disc 116 and opening 139 of LAA 136, reducing or eliminating peri-device leakage pathway 138.

Figure 7B:
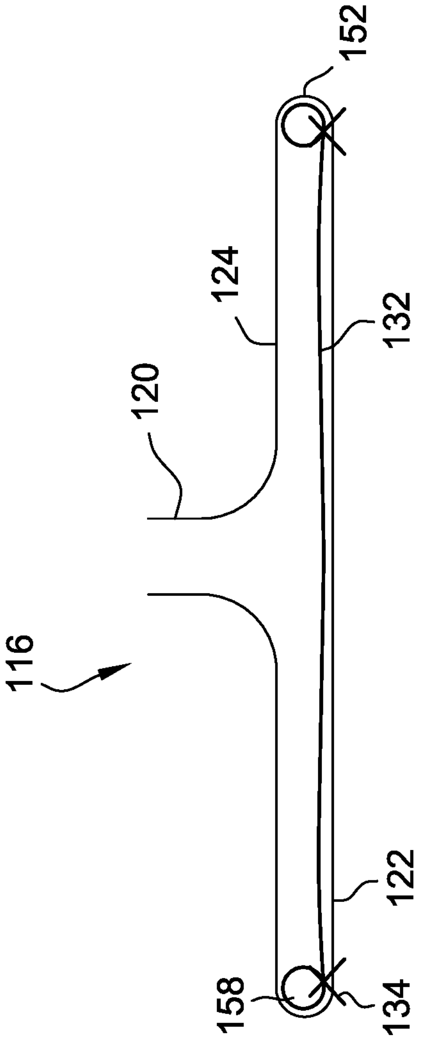
FIGS. 7A and 7B depict an additional and/or alternative fabric patch for use with the medical devices of the present disclosure.
Figure 7A:
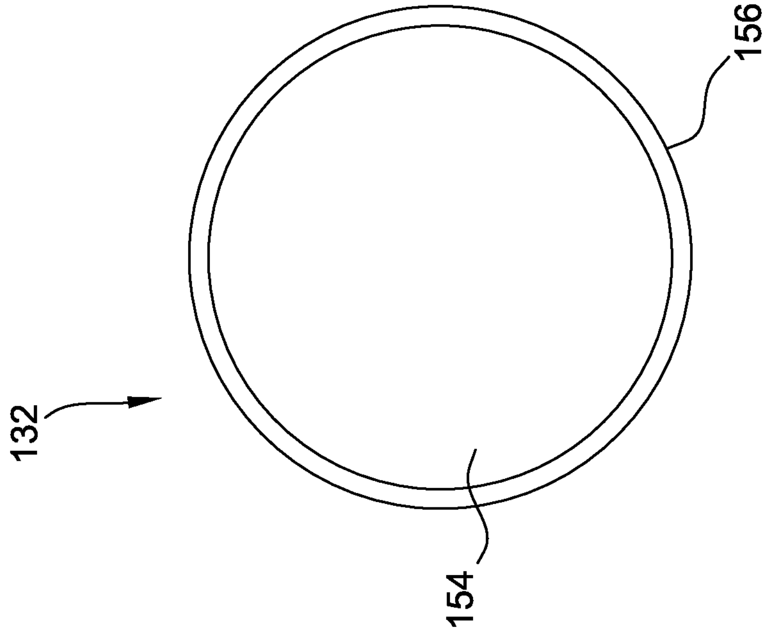

Medical device 110 as shown in FIG. 6 may include fabric patch 132 as illustrated in FIGS. 7A and 7B. In particular, in some embodiments, fabric patch 132 has a circular configuration and includes a first, circular portion 154 and a second, annular portion 156. Annular portion 156 extends from and/or is coupled to a peripheral edge of circular portion 154. Fabric patch 132 is coupled to disc 116 (e.g., proximal surface 122) by sutures 134, for example, along an interface between circular portion 154 and annular portion 156. In some embodiments, annular portion 156 is implemented as a flexible cylindrical rod 158. Flexible cylindrical rod 158 may be formed from any suitable material, including a fabric or yarn material. It is contemplated that the fabric or yarn material of flexible cylindrical rod may include polyester, polyethylene, or any other suitable material. Flexible cylindrical rod 158 may have a diameter from about 0.5 to about 2.0 millimeters. It is contemplated that the size of flexible cylindrical rod 158 may vary to ensure that flexible cylindrical rod 158 provides a desired increase in sealing effect to be provided by fabric patch 132 secured to disc 116. For example, in some embodiments, flexible cylindrical rod 158 has a diameter substantially equal to a depth or height of edge 123. In other embodiments, annular portion 156 may be formed from any other material, and may be coupled to or integral to circular portion 154.

Fabric patch 132 may be comprised of any suitable material that allows for fabric patch 132 to provide a sealing effect to medical device 110. Examples of suitable material may include but are not limited to polyester and polyethylene.

In one embodiment, medical device 110 (e.g., disc 116, lobe 118, connecting member 120) is formed from a shape-memory material. One particular shape memory material that may be used is Nitinol. Nitinol alloys are highly elastic and are said to be "superelastic," or "pseudoelastic." This elasticity may allow medical device 110 to be resilient and return to a preset, expanded configuration for deployment following passage in a distorted form through delivery catheter 104. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety. In one exemplary embodiment, medical device 110 (e.g., disc 116, lobe 118, connecting member 120) is formed from a braided shaped-memory material (e.g., a braided nitinol fabric or other mesh material, such as PE, PET, Si, PLLA, PLGA, PlA, PLLA-PLC, etc.), to provide an occlusive effect. Moreover, the braided mesh fabric material enables medical device 110 to be selectively transitioned from an expanded configuration to a collapsed configuration for delivery (e.g., through delivery catheter), and return to the expanded configuration upon deployment at the target site.

It is also understood that medical device may be formed from various materials other than Nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax™, nylon, polyurethane, silicone, PTFE, polyolefins and ePTFE. Additionally, it is contemplated that the medical device may comprise any material that has the desired elastic properties to ensure that the device may be deployed, function as an occluder, and be recaptured in a manner disclosed within this application.

Figure 8:
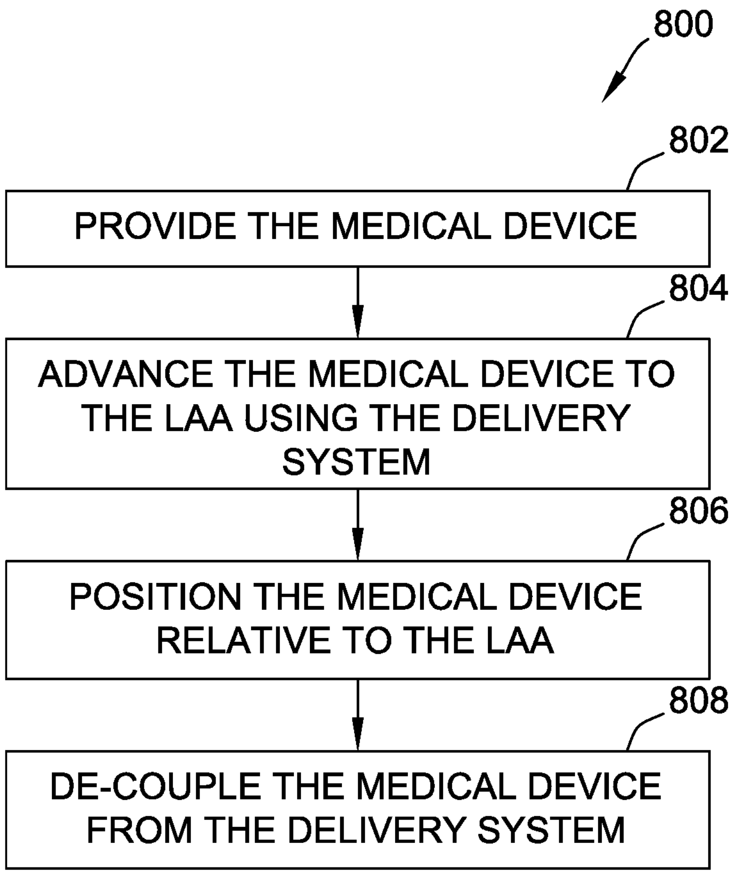
FIG. 8 is a flow diagram of a method of occluding a target site within a patient's vascular system with a device in accordance with the present disclosure.

Turning now to FIG. 8, a flow diagram of an exemplary method 800 of using medical device 110 to occlude an LAA in a patient is shown. In the exemplary embodiment, method 800 includes providing 802 a medical device. As described herein, the medical device includes a proximal end and a distal end, wherein the proximal end includes a disc and the distal end includes a lobe, wherein the disc and the lobe are connected by a connecting member, wherein the disc comprises a proximal surface, and a distal surface, wherein the lobe comprises a proximal surface, a distal surface, and a side surface extending between and connecting the proximal surface and the distal surface, and a fabric patch, wherein the fabric patch is coupled to the proximal surface of at least one of the disc or the lobe and to at least one additional surface of the at least one of the disc or the lobe.

Method 800 also includes advancing 804 the medical device to the LAA using a delivery system including a catheter and a delivery cable, positioning 806 the medical device relative to the LAA to occlude blood flow to and from the LAA, and de-coupling 808 the medical device from the delivery cable to deploy the medical device.

Method 800 may include additional, alternative, and/or fewer steps, including those described herein. For example, in some embodiments, positioning 806 the medical device relative to the LAA includes placing the lobe of the medical device within the body of the LAA and the disc outside of the LAA to abut the adjacent wall surrounding the opening of the LAA.

Additionally, de-coupling 808 the medical device from the delivery cable includes medical device transitioning from the constricted configuration adopted for delivery from a catheter to the preset expanded configuration.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a target site, the medical device comprising:

a proximal end and a distal end, wherein the proximal end comprises a disc and the distal end comprises a lobe, the disc having a greater diameter than the lobe, wherein the disc and the lobe are connected by a connecting member and the disc, the lobe, and the connecting member are formed from a same occlusive, braided shape memory material, wherein, when the medical device is deployed at the target site, the lobe is configured to be positioned within a tissue cavity and engaged with tissue within the tissue cavity, and the disc is configured to be positioned outside of the tissue cavity and engaged with tissue at an entrance to the tissue cavity, and wherein the disc comprises a proximal surface and a distal surface enclosing a first volume, and the lobe comprises a planar proximal surface, a planar distal surface, and a cylindrical side surface extending between and connecting the planar proximal surface and the planar distal surface of the lobe to enclose a second volume greater than the first volume, the planar proximal surface of the lobe being spaced substantially uniformly from the planar distal surface of the lobe; and a fabric patch, wherein the fabric patch (i) extends across an entirety of the planar proximal surface of the lobe and at least a portion of the cylindrical side surface of the lobe, (ii) is sutured to the braided shape memory material at a plurality of varying axial positions and a plurality of different circumferential locations along the cylindrical side surface of the lobe, and (iii) is configured to reduce or prevent leakage between the lobe and tissue even when a portion of the disc and a portion of the cylindrical side surface of the lobe are partially disengaged from the tissue.

2. The medical device of claim 1, wherein the fabric patch has a circular configuration and includes a circular first portion and an annular second portion coupled to a peripheral edge of the first portion.

3. The medical device of claim 1, wherein the fabric patch has a substantially circular configuration.

4. The medical device of claim 3, wherein the fabric patch has a diameter greater than a diameter of the lobe.

5. The medical device of claim 1, wherein the braided shape-memory material is selected from the group consisting of nitinol, stainless steel, CoCrMo alloys, and combinations thereof.

6. The medical device of claim 1, wherein the fabric patch is formed from polyester or polyethylene.

7. The medical device of claim 1, wherein the fabric patch extends along an entire axial length of the cylindrical side surface of the lobe.

8. The medical device of claim 1, wherein the fabric patch extends only across the surfaces of the lobe.

9. The medical device of claim 1, wherein the fabric patch extends along only a portion of an axial length of the cylindrical side surface of the lobe.

10. A delivery system for deploying a medical device to a target site, the delivery system comprising:

the medical device comprising:

a proximal end and a distal end, wherein the proximal end comprises a disc and the distal end comprises a lobe, the disc having a greater diameter than the lobe, wherein the disc and the lobe are connected by a connecting member and the disc, the lobe, and the connecting member are formed from a same occlusive, braided shape memory material, wherein, when the medical device is deployed at the target site, the lobe is configured to be positioned within a tissue cavity and engaged with tissue within the tissue cavity, and the disc is configured to be positioned outside of the tissue cavity and engaged with tissue at an entrance to the tissue cavity, and wherein the disc comprises a proximal surface and a distal surface enclosing a first volume, and the lobe comprises a planar proximal surface, a planar distal surface, and a cylindrical side surface extending between and connecting the planar proximal surface and the planar distal surface of the lobe to enclose a second volume greater than the first volume, the planar proximal surface of the lobe being spaced substantially uniformly from the planar distal surface of the lobe, and a fabric patch, wherein the fabric patch (i) extends across an entirety of the planar proximal surface of the lobe and at least a portion of the cylindrical side surface of the lobe, (ii) is sutured to the braided shape memory material at a plurality of varying axial positions and a plurality of different circumferential locations along the cylindrical side surface of the lobe, and (iii) is configured to reduce or prevent leakage between the lobe and tissue even when a portion of the disc and a portion of the cylindrical side surface of the lobe are partially disengaged from the tissue; and a delivery device comprising:

a delivery catheter;

a delivery cable within the delivery catheter and translatable with respect to the delivery catheter; and a coupling member configured to couple the medical device to the delivery cable for facilitating at least one deployment of the medical device at the target site.

11. A medical device for treating a target site, the medical device comprising:

a disc at a proximal end of the medical device, the disc comprising a planar proximal surface, a planar distal surface, and a side surface collectively enclosing a first volume;

a lobe at a distal end of the medical device, the lobe having a cylindrical shape and comprising a proximal surface, a distal surface, and a cylindrical side surface collectively enclosing a second volume greater than the first volume;

a connecting member connecting the disc and the lobe, wherein the disc, the lobe, and the connecting member are formed from a same occlusive, braided shape memory material; and a fabric patch having an initial condition and a use condition, the fabric patch in the initial condition having a star configuration including a circular central portion and a plurality of extensions extending radially outward from the central portion to respective free ends, wherein in the use condition of the fabric patch (i) the central portion is coupled to the planar proximal surface of the disc and extends across an entirety of the planar proximal surface of the disc, (ii) the plurality of extensions extend axially along the side surface of the disc such that the fabric patch extends along an entire axial length of the disc, and (iii) the plurality of extensions are coupled to the planar distal surface of the disc in an overlapping configuration in which the free ends of the plurality of extensions at least partially overlap one another.

12. The medical device of claim 11, wherein the central portion of the fabric patch has a diameter approximately equal to a diameter of the planar proximal surface of the disc.

13. The medical device of claim 11, wherein the fabric patch is coupled to the disc by sutures.

14. The medical device of claim 13, wherein the fabric patch is coupled to the disc by sutures positioned along the proximal surface and the distal surface of the disc.

15. The medical device of claim 14, wherein the fabric patch is coupled to the disc by sutures positioned along the side surface of the disc.

16. The medical device of claim 11, further comprising a flexible cylindrical rod positioned against an interior of the side surface of the disc.

17. The medical device of claim 16, wherein the flexible cylindrical rod has a diameter that corresponds to a depth of the disc, from about 0.5 to about 2.0 mm.

* * * * *